(12) United States Patent
Ihde

(10) Patent No.: US 7,556,500 B2
(45) Date of Patent: Jul. 7, 2009

(54) BONE-ADAPTIVE SURFACE STRUCTURE

(75) Inventor: Stefan Ihde, Uetliburg (CH)

(73) Assignee: Biomed Est. (LI)

(*) Notice: Subject to any disclaimer, the term of this patent is extended or adjusted under 35 U.S.C. 154(b) by 0 days.

(21) Appl. No.: 11/015,548

(22) Filed: Dec. 17, 2004

(65) Prior Publication Data
US 2005/0106535 A1 May 19, 2005

Related U.S. Application Data
(63) Continuation-in-part of application No. 10/714,200, filed on Nov. 14, 2003.

(30) Foreign Application Priority Data
Jun. 10, 2002 (DE) .................... 202 08 975 U
Nov. 15, 2002 (EP) ...................... 02090379

(51) Int. Cl.
*A61C 8/00* (2006.01)
(52) U.S. Cl. .............. 433/176; 433/173; 433/174; 433/175; 433/220; 623/16.11; 623/17.17
(58) Field of Classification Search ............ 433/173, 433/176, 220, 174, 175; 623/16.11, 17.17
See application file for complete search history.

(56) References Cited

U.S. PATENT DOCUMENTS

| | | | | |
|---|---|---|---|---|
| 4,302,188 A | * | 11/1981 | Driskell | ............... 433/173 |
| 4,344,757 A | * | 8/1982 | Streel | ............... 433/173 |
| 4,522,596 A | * | 6/1985 | Ashkinazy | ............... 433/173 |
| 4,538,304 A | * | 9/1985 | Grafelmann | ............... 433/176 |
| 4,768,956 A | * | 9/1988 | Kurpis | ............... 433/173 |
| 4,802,847 A | * | 2/1989 | Komatsu | ............... 433/176 |
| 4,842,517 A | * | 6/1989 | Kawahara et al. | ............... 433/173 |
| 4,964,801 A | * | 10/1990 | Kawahara et al. | ............... 433/173 |
| 5,489,306 A | * | 2/1996 | Gorski | ............... 623/23.55 |
| 5,965,006 A | * | 10/1999 | Baege et al. | ............... 205/666 |
| 6,186,791 B1 | * | 2/2001 | Karmaker et al. | ............... 433/220 |
| 6,277,149 B1 | * | 8/2001 | Boyle et al. | ............... 623/17.16 |
| 6,364,663 B1 | * | 4/2002 | Dinkelacker | ............... 433/173 |

OTHER PUBLICATIONS

Scortecci, Gerard DMD, *Disk Implant System™, Results in Resorbed Maxilla with Immediate Load*, Apr. 2001, International Magazine of Oral Implantology, Case Report, pp. 18-26.

* cited by examiner

Primary Examiner—Cris L Rodriguez
Assistant Examiner—Michael R Ballinger
(74) Attorney, Agent, or Firm—Robert C. Haldiman; Husch Blackwell Sanders LLP

(57) ABSTRACT

Bone-adaptive surface structures are provided for lateral jaw implants. Micromechanical and/or macromechanical surface structures having various body forms are incorporated into selected segments of the surface of a base and of a bar that connects a shaft with the base to accelerate the healing process after the implant is inserted into the jaw bone and to make a critical improvement in holding the implant firmly in place without rotation. A process of manufacturing the surface structures includes forming a macromechanical surface on the implant to increase its surface area; and superimposing micromechanical canals on the macromechanical surface, the canals having a size smaller than the minimum size of the osteons in the bone into which the implant is to be inserted.

36 Claims, 3 Drawing Sheets

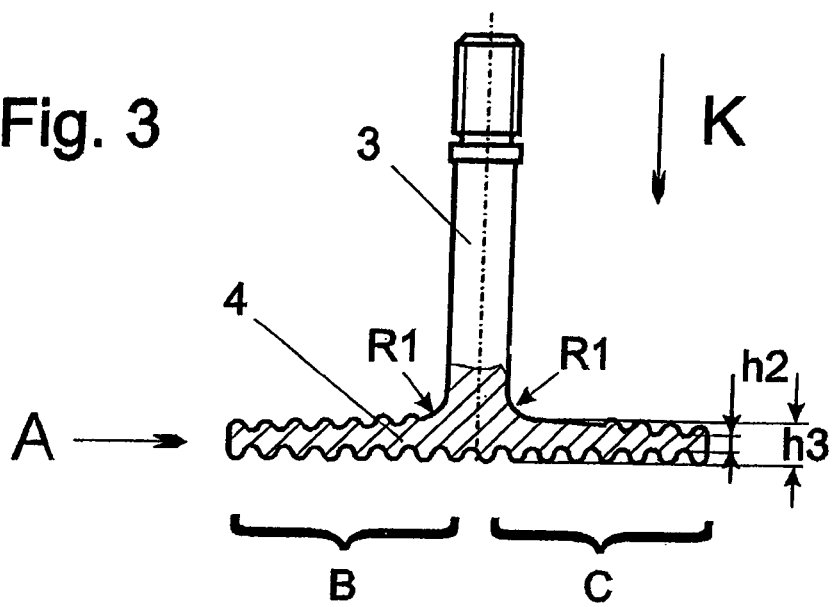
Fig. 3
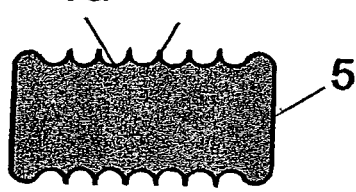
Fig. 4
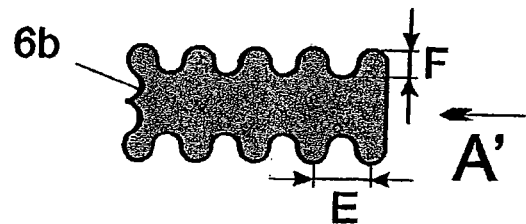
Fig. 5
Fig. 7
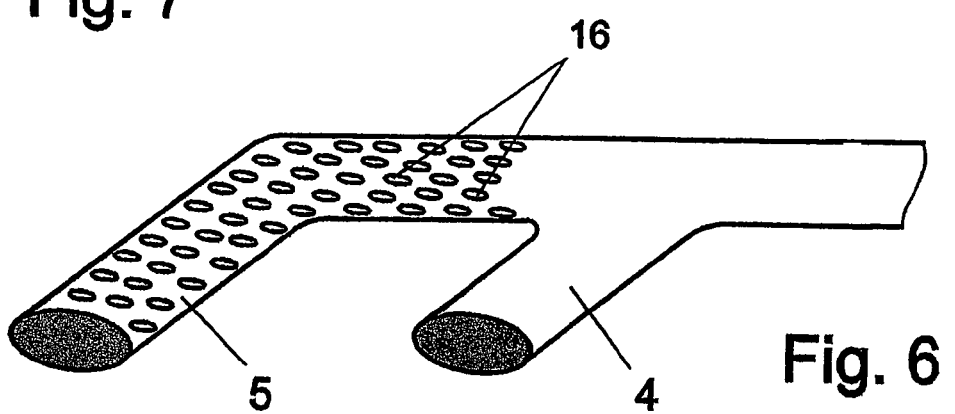
Fig. 6

BONE-ADAPTIVE SURFACE STRUCTURE

CROSS REFERENCE TO RELATED APPLICATIONS

This application is a continuation-in-part of pending U.S. application Ser. No. 10/714,200 filed Nov. 14, 2003, and claims priority of EP 02090379.5 filed Nov. 15, 2002, which claims priority to DE 20208975 U filed Jun. 10, 2002.

TECHNICAL FIELD OF THE INVENTION

The invention concerns bone-adaptive surface structures for orthopedic implants, particularly lateral jaw implants (basal osseointegration); that is, for implants which are inserted into the jaw from the side, and which are also known as "disk implants."

DESCRIPTION OF THE RELATED ART

Various industrially produced implants have been used for decades in dental implantology. These include cylinder implants, screw implants, leaf implants, and disk implants. Individually produced subperiostal implants also play a part.

These implants developed from a kind of box shape. They generally have a disk-shaped implant base. U.S. Pat. No. 3,925,892 (Juillet) describes an implant with a rectangular base and a post screwed onto it. Then the crown or the prosthesis is fastened to the post. French patent 2 302 715 (Clune-Cost) describes a one-piece implant. According to U.S. Pat. No. 4,722,687 (Scortecci) a congruent osteotomy instrument was developed later, as well as an osteotomy tool which simultaneously served as its own implant, and so was left in the bone (U.S. Pat. No. 4,815,974). Later, U.S. Pat. No. 4,344,757 described other possible forms, as did U.S. Pat. No. 4,964,801 (Kawahara), EP 0 935 484 A1 (Ihde), etc.

All the developments mentioned above had in common the fact that they essentially improved the geometry, or the external shape, of the implants. That contributed to a broader range of possible uses, lower fracturability, and better retention.

SUMMARY OF THE INVENTION

The strongest possible hold in the jawbone is an essential objective of any implant. Aside from the variously shaped bases intended to help the implant grow into the jaw bone and improve its firm seating, surface structures intended to improve the holding of the implant have been discussed quite recently. These involve combinations of air abrasion ("sandblasting") processes with etching processes. Etching has the additional objective of removing residue from mechanical processing and abrading from the surface of the implant. These processes treat the surface at the microscopic level.

Although at least some of the prior art implants have worked well, further acceleration of the healing process of the implant into the jawbone after its insertion is desirable. Critically improving the anti-rotational retention of the implant is also desirable. The present invention is directed to providing a lateral implant which meets one or more of these goals.

SUMMARY OF THE INVENTION

According to the present invention there is provided a lateral jaw implant that has a surface enlargement including macromechanical bone adaptive surface structures worked into selected sections of the base. In one preferred arrangement the bone adaptive surface structures are periodic.

It has been found that significant improvements of the retention of the implant can be achieved by lateral implants, by means of macromechanically acting surface structures and even macromechanical surface forming, independent of the geometry of the implant body. At first glance, it appears impossible to apply macromechanical surface structures to lateral implants. It was determined that the implant bed prepared in the jawbone from laterally must be very thin, so that the blood supply is not too seriously impaired and so that primary bone healing is possible. Surprisingly, it was later found that having a surface structure in the form of grooves with profiles which are corrugated, pointed, or sawtooth-like, and which are arranged in parallel, concentric with the shaft, or in the form of a spiral form on the upper and/or the lower surface of the base, and which can at least in part extend onto the bar of the implant, can be inserted relatively easily if the height of the osteotomy slot does not exceed the core height $h_2$ of the surface structure. After insertion of the implant, the surface structures force themselves into the jawbone. This is promoted by the force of chewing, because the surface structures are perpendicular to the masticatory force. These basal osseo implantations differ from the situation with crestal (screw) implants, in which the threads, etc., lie transversally to the direction of chewing.

It has been determined from histological sections that small particles of bone are scraped off the jawbone during the insertion into the depressions of the surface structures. That avoids formation of voids, and the bone particles that are scraped off substantially accelerate the healing process.

Histologic examinations have also shown that the jawbones optimally tolerate contact of the basal structures of implants having a macromechanical surface structure. If the depth F of the macromechanical surface structure is from 0.05 to 2 μm, direct bone contact with the implant occurs (osseointegration). It is therefore unnecessary to apply an additional microstructure, such as, for example, titanium coatings applied by plasma spraying. Dispensing with such measures not only reduces cost, but also prevents the layers applied from producing supplemental microstructure separating from the surface during insertion of the implant, or later, thus causing inflammation and symptoms resembling polymetallosis.

According to an advantageous further development, the surface structures are worked into the base of the implant only in selected annular regions. Such implants present a situation in which only the annular regions with the enlarged surfaces are osseointegrated, while all the other regions experience only moderate osseointegration or are overgrown with connective tissue. This implant configuration is particularly advantageous for use in the vicinity of the maxillary sinuses. In this case the surface of the part of the implant in the vicinity of the maxillary sinus is smooth, resulting in very good self-cleaning, while the cortically anchored regions, i.e., the annular regions, have enlarged surfaces and so are integrated better. In this embodiment, supplemental microstructure of the surfaces by etching, air-abrading, etc., is again not necessarily required with this embodiment of lateral implants.

The advantageous effects noted above also appear if the surface structure consists of bowl-like depressions. The surface structures can be formed by variously shaped depressions and milled-out regions worked into the marginal zones of the base. In this variant embodiment, the geometry of the depressions, which differ from each other, should advantageously be selected such that the forms of the depressions in contact produce a configuration with reentrant angles. Furthermore, the substrate can in turn be formed so that it ends in the peripheral region of the base with a core height of $h_2$.

Aside from the advantages noted which are also attainable with this solution, the peripheral depressions in the base substantially improve the in-growth because the jaw bones tend to close, reaching and filling out the depressions with smaller configurations sooner than those with somewhat larger configurations. In this way, a high initial strength can be attained considerably sooner.

If lateral implants also have elastic properties, then the threaded parts sink into the spongy bones under stress. That results in a tension directed centrally on the threaded parts. In this situation, the surfaces of the previously known lateral implants can tear out of the bone combination. However, due to the surface structures according to the invention, it is possible to maintain the combination with the bone even under large stresses. Thus individual implants can be more heavily loaded, with the result that fewer implants per jaw are needed to reproduce the ability to chew. In this way, even severely atrophied jaws can be cared for without bone grafting.

With proper selection of microdimensions and macrodimensions, it is possible to provide an implant which fits biomechanically into the bone but is still easily insertable, and which has a surface structure that offers the implant optimal macromechanical hold in the jawbone. Then the vertically acting masticatory forces are absorbed in an astonishing manner by the likewise vertical structures such as, for example, the grooves made in the surface of the implant base and/or bar.

It is also possible to elevate the surface structure by sintering one or more layers of balls of titanium or a titanium alloy having a diameter of 120 to 220 μm onto the desired surfaces of the implant. This likewise provides higher surface roughness without additional micromechanical measures such as those described above.

From extensive series of histological examinations and cracking tests, it has been found that the best results for adhesion are attained with the dimensions shown below for the bases and surface structures:

Implant diameter D/implant width: 8-15 mm
Height h3 of the implant base where it joints the shaft: 0.7-1.2 mm
Distance E between the peaks of the surface structure: 0.2-0.7 mm
Width G of the ring for the implant base: 1.0-2.4 mm
Core height h2: 0.6-0.9 mm
Depth F of the surface structure: 0.05-0.4 mm.

Lathe-turning or milling processes, or a combination of those two processes, are particularly suitable for producing implants according to the invention. The well-known air-abrading or etching processes are used advantageously for final working.

In further tests it was found that bonding strength to bone can be even further increased if a microstructure overlays the above described macromechanical structure. This microstructure comprises a net of longitudinal grooves or canals over the whole endosteal surface of the implant. Contrary to the beliefs of the dental profession, further histological investigation has shown that a strong, long-lasting, bone-to-implant adhesion can be achieved not only by large areas of bone to implant contact, but also through a second expedient. The expedient is that small implant-to-bone areas may serve as well for transmitting large forces, if the bone which is in contact to the implant is well nourished from all sides. This nourishment is performed through canals which underlie the macrostructure. It is especially advantageous if those canals, which are confluent in all directions, are equipped with a very smooth surface. The surface is preferably smooth or polished to avoid or reduce the threat of bacterial contamination.

The very smooth surface structure can be produced in a particularly elegant manner using ablative laser processes. This type of production also favors production of bowl-like surface structures. Hence milling or turning procedures or even laser molding of the surface is used to create the macrostructure of the implant, whereas the confluent and continuing canals, which cover the whole endosseous surface, are carved out by means of laser energy. The surface creates the possibility of passive nutrient diffusion by creating a 3-D surface which allows flow perfusion underneath the integrated bone area virtually from "inside" the implant.

It is especially advantageous to apply the surface as per onto the rings and peaks of the lateral implants, because the rings are placed in cortical areas of the jaw bone. Those areas will be again turned into cortical bone after healing. Since cortical bone does not contain any blood vessels, good circulation of nutritients over the new, canal-bearing surface, will allow easy microcirculation underneath the osseointegrated surface areas. It is true and it was found in histological tests that the microcirculation may break down during the later phase of use of the implant. This is owed to the fact that bone shows creep and plastic deformation over the time and hence some of the wells may be stuffed later with particles of bone by functional forces or events creating plastic deformation rather than by active ingrowth. Especially advantageous are canals, which show an undercut and being smaller than the size of an osteon of the relevant bone area, because bone will not be able to colonize those areas by active growth at all.

The optimum size of the canals or undercuts is not nominated in mm; however the size of the undercuts and canals is smaller than the size of osteons in the bone into which the surface is implanted. This is important, because it is known that secondary osteons are considerable larger in the human femur than in human ribs. The physician should determine the minimum size of secondary osteons from experience or literature, or from investigating into the actual patient's microanatomical situation.

The micromechanical surface is hence not intended to keep a distance forever between the osseointegrated parts of the implant and the core of the implant. The intention is to allow microcirculation in the initial phase of healing which may last several weeks to months. During later phase of the mentioned healing period, masticatory loads may be applied to the implant.

One advantageous way of creating the desired surface properties is a two step procedure: during the first operation peaks are milled out or cut out or melted out, preferably leaving round bases without corners, and second the peaks are melted to become round and having undercuts by electrically driven power, namely laser forces or microplasma soldering devices. By this process the sintering of several layers of balls made from implantable material, which would achieve the same intentional result, can be avoided.

Another advantageous way of achieving the invented surface is that the second operation comprises applying mechanical pressure, also in combination with a rotation procedure. This will bend and/or deform the peaks of the structures which have been created by the first operation.

The above-described surface production technique is not limited to lateral dental implants; it may be used also for crestal implants, screw, and blade implants. And the surface can be applied to orthopedic implants which are intended to integrate onto bone with the same beneficial results.

Applying the new surface to lateral dental implants, however, brings additional benefits compared to massive, crestal types of implants (i.e. screws, blades). Due to their design and due to the fact that the base plate hangs between the two corticals of the jaw bone, lateral implants show some possibilities of elastic movement within the bone. The movements are induced by masticatory forces, especially by chewing. Rhythmical motions of the jaw bones support the fluctuation of liquids underneath the integrated surface by creating a repeated pumping effect. Just as this effect could enhance fluctuation within osteons, the new surface allows fluctuation between the implants and the integrating bone surface. Implants, which show structural elasticity, distribute forces over an increasing area with the force increasing and they distribute forces over time. Strong, sharp impact of forces on small bone areas is thus avoided. Elasticity can be by design through choice of materials, thickness, and design of struts and bars. The elastic motions increase fluctuations and through this effect increase nutrition of bone which leads to fast bone growth and to stronger integration in shorter time.

BRIEF DESCRIPTION OF THE DRAWINGS

Reference is now made more particularly to the drawings which illustrate the best presently known mode of carrying out the invention and wherein similar reference characters indicate the same parts throughout the several views.

FIG. 3 is a section taken generally along line M-M and through the bar of the implant shown in FIG. 2, and showing an arrangement of the surface structure.

FIG. 4 is a cross section of a base embodying a surface structure having points and valleys.

FIG. 5 is a cross section of a base embodying a corrugated surface structure, and with a pointed surface structure provided in the inner wall area of the base.

FIG. 6 is a partial perspective view of a base having a surface structure with bowl-like indentations.

FIG. 7 is a cross section of a base with a sawtooth-like surface structure.

DETAILED DESCRIPTION

Figure 1A:
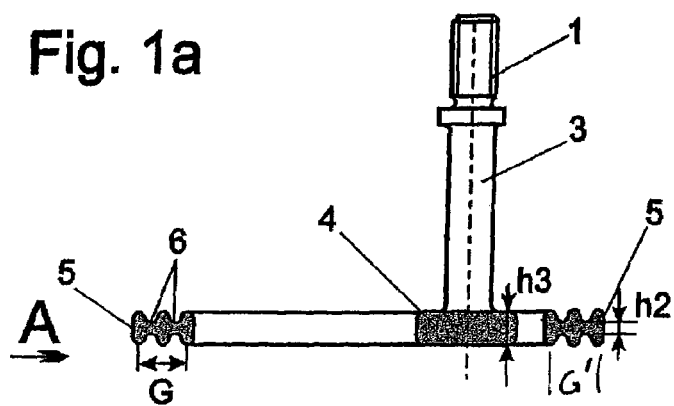
FIG. 1a is a longitudinal section taken generally along line L-L of FIG. 1b.
Figure 1B:
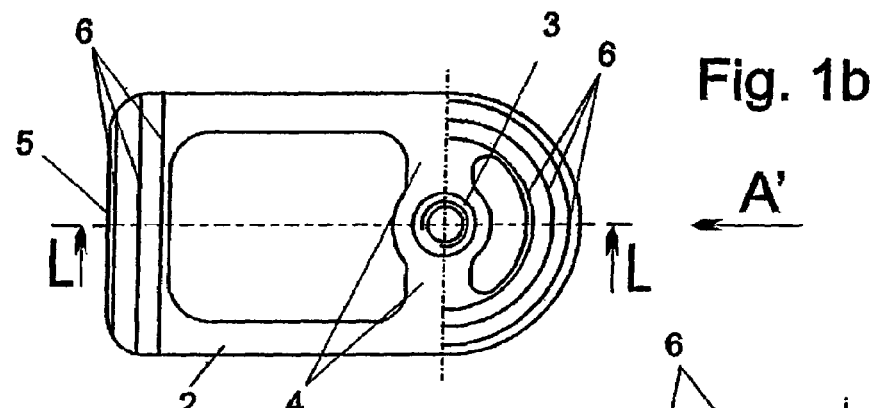
FIG. 1b is a plan view of a bone-adaptive lateral jaw implant having surface structures embodying the invention and with a partial rectangular base.

As can be seen in FIG. 1a, a screw thread 1 is provided at a distal end of a shaft 3 for connecting with a prosthesis (not shown). The thread can be an internal or external thread. In appropriate circumstances the prosthesis can be adhesively secured, as by an epoxy. FIG. 1b shows a base 2 in the form of an annular body of a lateral dental implant. A bar 4 connects the shaft 3 to the base 2. It has been determined that implants of this type transfer the masticatory force essentially into the peripheral annular section of the base 2, indicated here by 5, which is anchored in the cortical jaw bone. As shown in FIGS. 4, 5 and 7, numerals 6a, 6b and 6c indicate various surface structures embodying the invention that may be on the base 2.

Figure 2:
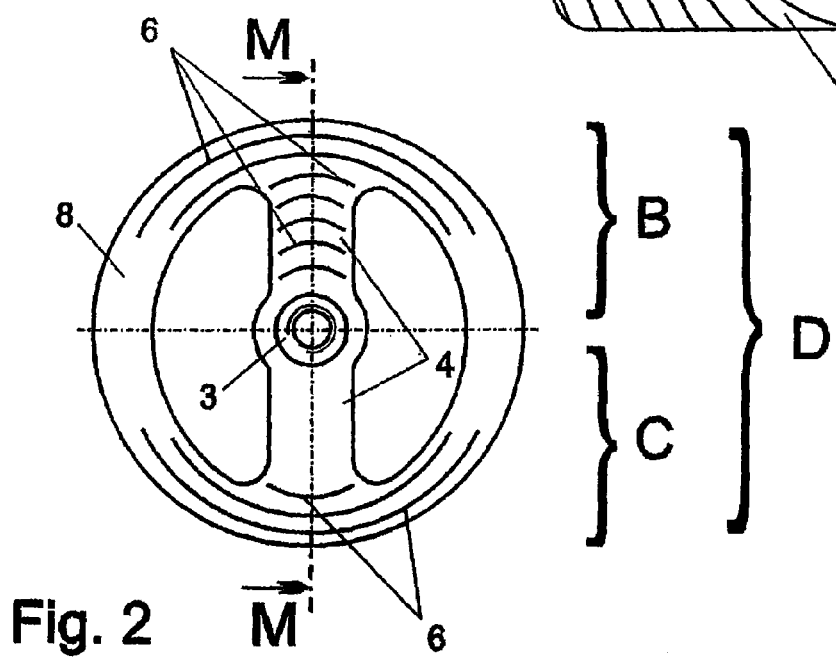
FIG. 2 is a plan view of a lateral jaw implant having a round base.

In FIG. 1a, the letter G indicates the width of an outer ring of the base 2 or of a base 8 (see FIG. 2).

In the embodiment shown in FIG. 1b, the surface structures are formed by periodic grooves 6 which can run parallel with each other, as shown at the left of the shaft 3, or concentrically, as shown at the right of the shaft 3. The term "periodic" means that the grooves 6 occur at regular intervals, or intermittently. It should be understood that some irregularity of occurrence is intended also to be included within the meaning of the term.

Figure 1C:
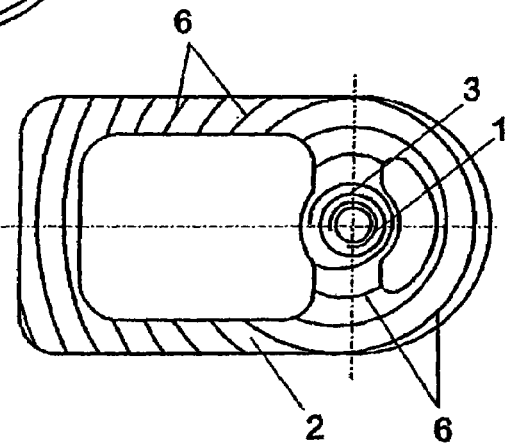
FIG. 1c is a plan view of a lateral jaw implant having surface structures with a spiral design and arrangement.

In the embodiment shown in FIG. 1c, the periodic surface structures 6 (which can have a profile such as shown in FIGS. 4, 5 or 7) have a spiral shape and extend essentially over the entire upper and/or lower surface of the base 2, with the center of the spiral placed in the region where the shaft 3 connects to a bar 4, advantageously a cross bar.

FIG. 2 shows another variant in the form of a lateral dental implant having a round base 8. Pointed surface structures 6a, or 6c, or corrugated surface structures (see FIG. 1a or 5) are formed by the grooves 6 which may be located on the outer ring and on the bar 4 as far as the shaft 3 in the upper part B of FIG. 2. One alternative arrangement is shown in the lower part C of FIG. 2 where the grooves 6 extend only to the junction of bar 4 with the base 8. The latter of the two embodiments has the advantage that this design increases the breaking strength of the base 2 in the vicinity of the bar 4. The letter D indicates the diameter of the round base 8. Thus round implants are symmetrical; while there can be numerous dimensions for elongate implants or different diameters for round implants with multiple force-transferring bases.

In FIG. 3, the top surface structures continue up to the shaft 3 at the left part B; while in the right part C they terminate about midway between the periphery of the base and the shaft 3. Therefore, a central height h3 (or thickness) of the base 8 near its juncture with shaft 3, and a core height h2 (or inner thickness) resulting from the corrugations are arranged so that the surface structures embodying the invention have either apexes which maintain the central height h3 or, as shown in the right part C, diminish outwardly and are less high in the peripheral region of the base 2. It is also possible for the surface structure in the peripheral region to have a height which exceeds the central height h3 of the base 8 or 2, or the surface structure which terminates in the vicinity of the junction of the shaft 3 and bar 4 at the implant height h3. In this event, there may be a continuous decrease of the depth of the selected profile shape from the periphery to the shaft 3.

Figure 8:
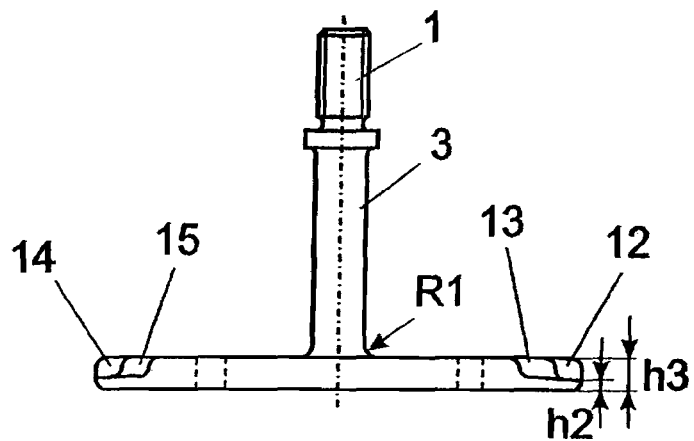
FIG. 8 is a front view of the lateral jaw implant shown in FIG. 9.

In FIGS. 3 and 8, R1 indicates the radius of the transition from the shaft 3 to the bar 4. The letter K in FIG. 3 indicates the direction of the principal masticatory force. However, forces that occur with laterotrusion motions during the act of chewing also act at an angle, even perpendicular (as indicated by the letter A), to the main masticatory force.

FIG. 4 shows a bone-adaptive surface structure with a profile in which the apexes terminate in points, while the substrate or the wave valleys 7a have essentially a round concave shape.

FIG. 5 shows another optimized variant for the shaping of the surface structure which is also inserted in the vertical sidewall surface of the force-transferring base 2 or 8. The advantageous shaping of such structures 6b on the outer side of the implant in particular is being proven clinically. The letter A' indicates a direction opposite to the path of inserting the implant. The distance between corrugations or points of the surface structure is indicated by the letter E; while the depth of the macromechanical surface structure is indicated by the letter F. According to the results of the investigations on which this application is based, the distance E is optimally 0.2-0.7 mm.

FIG. 6 shows a portion of the base 4 in which the surface structure embodying the invention is formed by bowl-like depressions 16 made by milling, by lasers, or a similar process. Investigations have determined that the depth of these depressions is preferably 0.05-0.25 mm. Greater depths retard osseointegration, while lesser depths do not give good results for bone adherence of the implant. The bowl-like depressions 16 result in circumjacent individual elevations around the depressions which form the crest of the surface structure.

As shown in FIG. 7, surface structures with edges 10 perpendicular or approximately perpendicular to the direction of insertion and slowly diminishing concave sides 11 also give particularly good adhesion values. These sawtooth-like structures can be produced either just over the annular region of the base or over the entire implant. However, for reasons of production technology, it can be difficult to provide truly perpendicular edges because the initially vertical edges formed by lathe-turning or machining can be flattened by ablative abrading. In production, the result is that the angles are between 80 and 90 degrees, but they all give good clinical results.

Figure 9:
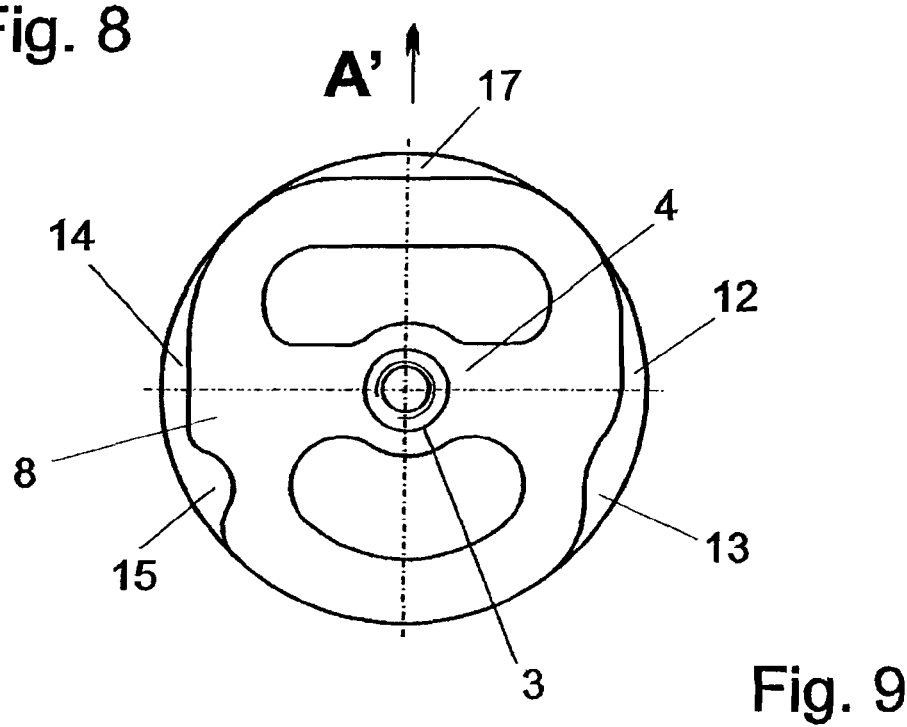
FIG. 9 is a plan view of a lateral jaw implant having elongate depressions worked into the peripheral area of its base.
Figure 10:
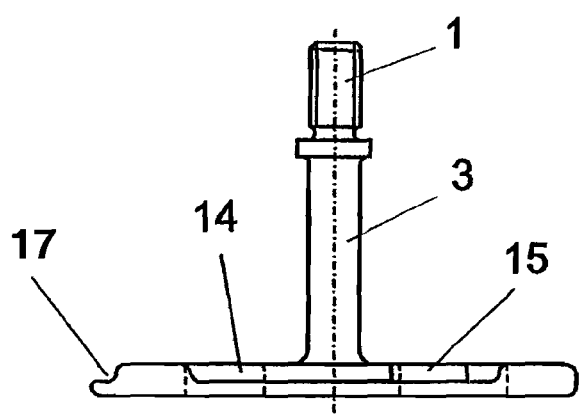
FIG. 10 is a side view of the lateral jaw implant of FIG. 9 as seen from the left thereof.

In the embodiment shown in FIGS. 8 to 10, elongate recesses or depressions 12, 13 and 14, 15 are made in the base 8 of the lateral dental implant. They each have a different configuration, in that the geometries that deviate from each other are selected so that there is a reentrant angle between the forms of the adjacent depressions 12, 13 and 14, 15. Following insertion of the implant into the ground osteotomy slot, the jaw bone, which has the tendency to draw together, will reach into the lesser depressions 12 and 14 more quickly than into the depressions 13, 15 with the greater shaping. In this way, high initial strength is attained relatively rapidly, with the bone particles scraped off during the insertion and collected in the depressions 13, 15 promoting bone formation and healing of the implant. The depression 17, directed toward the insertion side of the implant and preferably placed obliquely, makes it easier to insert the implant into the osteotomy slot. The insertion is made in the direction of arrow A'.

As indicated above, the surface structure is, in the first instance a macromechanical surface structure as illustrated in FIGS. 4, 5 and 7, for example. Milling or turning procedures or even laser molding of the surface is used to create the macrostructure of the implant. In the second instance a micromechanical surface structure may be superimposed or overlaid. This microstructure comprises a net of longitudinal grooves or canals over the whole endosteal surface of the implant. It is especially advantageous if these canals, which are confluent in all directions, are equipped with a very smooth surface to abate bacterial contamination and allow perfusion of the bone adjacent the implant. The very smooth surface structure is produced using ablative laser processes. Hence, the confluent and continuing canals, which cover the whole endosseous surface, are carved out by means of laser energy.

An additional continuous web of canals can cover those parts of the surface of the implant which are intended to reach osseointegration. The canals can have a depth in the range of 0.05-0.50 mm and smooth surfaces so that initial bone in growth is retarded.

The optimum size of the canals or undercuts is smaller than the size of osteons in the bone into which the surface is implanted. This is important, because it is known that secondary osteons are considerable larger in the human femur than in human ribs. The physician should determine the minimum size of secondary osteons from experience or literature, or from investigating into the actual patient's microanatomical situation. This is not limited to lateral dental implants; but may be used also for crestal implants, screw, and blade implants. Further, the micromechanical surface structure can be applied to orthopedic implants which are intended to integrate onto bone with the same beneficial results.

One advantageous way of creating the desired surface properties is a two step procedure: during the first operation peaks are milled out or cut out or melted out, preferably leaving round bases without corners, and second the peaks are melted to become round and having undercuts by electrically driven power, namely laser forces or microplasma soldering devices.

Another advantageous way of achieving the desired surface is that the second operation comprises applying mechanical pressure, also in combination with a rotation procedure. This will bend and/or deform the peaks of the structures which have been created by the first operation and form the canals or undercuts.

In one embodiment of the present invention, the prosthetic device base has a first height and a second, shorter height with the second, shorter height being at a marginal zone. The marginal zone is substantially along a portion of a periphery of the base. The prosthetic device may have a marginal zone whose radial depth varies along the periphery of the base. The marginal zones may comprise reentrant angles. The marginal zones may form a depression relative to either the top surface or the bottom surface of the base and may be flush with the other of the top surface or the bottom surface. Some of the marginal zones may form depressions in either the top surface or the bottom surface.

The invention in its broader aspects is not limited to the specific steps, processes and apparatuses shown and described, but departures may be made therefrom within the scope of the accompanying claims without departing from the principles of the invention and without sacrificing its advantages.

What is claimed is:

1. A prosthetic device for implanting in bone comprising:
   a shaft said shaft having a first end and a second end;
   said first end having a mount for a dental device to be implanted;
   said second end being attached to a base;
   said base being substantially orthogonal to said shaft in at least two non-parallel directions, said base being substantially planar; at least one of a top surface or a bottom surface of said base having at least one apex and at least two valleys, said valleys being adjacent said apex, said apex and said valleys defining a macrostructure dimension, said macrostructure dimension being greater than the size of an osteon at a site of implantation;
   at least one of said surfaces having a surface including canals, said canals defining a microstructure dimension, said microstructure dimension being less than the size of an osteon at a site of implantation; and
   said valleys being at a marginal zone;
   said marginal zone being substantially along a portion of a periphery of said base; and
   said marginal zone having a radial width varying along said periphery of said base.

2. A prosthetic device according to claim 1, characterized in that said apex and said valleys are concentric with the shaft.

3. A prosthetic device according to claim 1, characterized in that said apex and said valleys are on the underside of the implant on the side away from the shaft.

4. A prosthetic device according to claim 1, characterized in that at least one apex and at least one valley are worked into a circumferential wall surfaces of the base.

5. The prosthetic device of claim 1 wherein said macromechanical surface comprises a depth of from about 0.1 mm to about 0.4 mm and said micromechanical surface comprises a depth between about 0.05 and 0.1 mm.

6. A prosthetic device for implanting in bone comprising:
a shaft said shaft having a first end and a second end;
said first end having a mount for a dental device to be implanted;
said second end being attached to a base;
said base being substantially orthogonal to said shaft in at least two non-parallel directions, said base being substantially planar; at least one of a top surface or a bottom surface of said base having at least one apex and at least two valleys, said valleys being adjacent said apex, said apex and said valleys defining a macrostructure dimension, said macrostructure dimension being greater than the size of an osteon at a site of implantation;
at least one of said surfaces having a surface including canals, said canals defining a microstructure dimension, said microstructure dimension being less than the size of an osteon at a site of implantation; and
a bar, said bar having a height that decreases from a region where said bar joins said shaft towards a peripheral height, a depth between said adjacent ones of said apexes and said valleys decreasing with the decreasing peripheral height.

7. The prosthetic device of claim 6 wherein said apex and said valleys alternate periodically.

8. The prosthetic device of claim 6 wherein said apex and valleys alternate to comprise corrugation.

9. The prosthetic device of claim 6 wherein said apexes have sharp edges oriented outwards from said top or bottom surface.

10. The prosthetic device of claim 6 wherein said valleys have rounded troughs, each of said troughs being concave.

11. The prosthetic device of claim 6 wherein the period of the apexes and valleys varies.

12. The prosthetic device of claim 6 wherein said apex-is a spiral.

13. The prosthetic device of claim 12 wherein said spiral centers on said shaft.

14. The prosthetic device of claim 6 wherein said valleys are generally parallel.

15. The prosthetic device of claim 6 wherein said valleys comprise bowl-like depressions.

16. The prosthetic device of claim 15 wherein said depressions have a depth in a range from about 0.05 millimeters to about 0.4 millimeters.

17. The prosthetic device of claim 6 wherein said base is curvilinear in shape.

18. The prosthetic device of claim 6 wherein said base has a substantially rectangular portion.

19. The prosthetic device of claim 6 wherein said base is curvilinear in part and substantially rectangular in part.

20. The prosthetic implant of claim 6 wherein said valleys are curvilinear and concave on a first side of each valley, and substantially vertical on an opposing side of each valley.

21. The prosthetic device of claim 6 wherein a height of said apex varies radially.

22. The prosthetic device of claim 6 wherein a width of one of said valleys is between about 0.2 and about 0.7 mm.

23. A prosthetic device according to claim 6, characterized in that a surface structure is a sawtooth profile with a front side running approximately perpendicular to the direction of insertion of the implant, and a concave rear side which terminates at the foot of the next subsequent perpendicular front side.

24. A prosthetic device according to claim 6, characterized in that a depth between said apex and said valley is 0.05-0.4 mm for an implant diameter of 8-15 mm and a height of the base of 0.7-1.2 mm.

25. A prosthetic device according to claim 6, characterized in that the distance between valleys is 0.2-0.7 mm.

26. A prosthetic device according to claim 6, characterized in that said apex and said valleys are on an upper side of the implant, the same side as is the shaft.

27. A prosthetic device according to claim 6, further comprising one or more layers of particles of titanium or a titanium alloy or other implantable material having a diameter of 120-220 μm that are tightly connected or sintered onto the surface of the base.

28. A prosthetic device according to claim 6, characterized in that said canals have a smooth surface, whereby initial bone ingrowth is retarded.

29. A prosthetic device according to claim 6, characterized in that the canals have a depth in a range from about 0.05 to 0.1 mm.

30. A prosthetic device according to claim 6, characterized in that said canals are formed by a laser.

31. The prosthetic device of claim 6 wherein said macromechanical surface comprises a depth from about 0.05 mm to about 0.4 mm.

32. The prosthetic device of claim 6 wherein said micromechanical surface comprises a depth between about 0.05 mm to about 0.1 mm.

33. The prosthetic device of claim 6 wherein said macromechanical dimension is from about 0.1 mm to about 0.4 and a depth of said canals is between about 0.05 and 0.1 mm.

34. The prosthetic device of claim 6 wherein said canals are superimposed over said apex and said valleys.

35. The prosthetic device of claim 6 having apexes and valleys on both a top surface and a bottom surface of said base.

36. The implant of claim 6 wherein said macrostructure has a width of about 0.2 to about 0.7 mm.

* * * * *